(12) United States Patent
Tsuchida et al.

(10) Patent No.: US 6,965,049 B2
(45) Date of Patent: Nov. 15, 2005

(54) ZWITTERIONIC LIPID COMPOUND AND USES THEREOF

(75) Inventors: Eishun Tsuchida, Tokyo (JP); Shinji Takeoka, Tokyo (JP); Keitaro Sou, Tokyo (JP); Katsura Mori, Yokohama (JP)

(73) Assignee: Oxygenix Co., Ltd., Tokyo (JP)

( * ) Notice: Subject to any disclaimer, the term of this patent is extended or adjusted under 35 U.S.C. 154(b) by 0 days.

(21) Appl. No.: 10/782,851

(22) Filed: Feb. 23, 2004

(65) Prior Publication Data

US 2004/0162261 A1 Aug. 19, 2004

Related U.S. Application Data

(63) Continuation of application No. PCT/JP02/08419, filed on Aug. 21, 2002.

(30) Foreign Application Priority Data

Aug. 24, 2001 (JP) .......................... 2001-254733

(51) Int. Cl.$^7$ ............................ C07C 229/00
(52) U.S. Cl. .................. 560/170; 560/169; 560/171; 560/123; 424/450
(58) Field of Search ................. 560/169, 170, 560/171, 123; 424/450

(56) References Cited

U.S. PATENT DOCUMENTS 5,370,877 A * 12/1994 Rosenberg et al. ......... 424/450

FOREIGN PATENT DOCUMENTS

WO    WO 02/38530    5/2002

OTHER PUBLICATIONS

Seong et al., Polymer Preprints, vol. 41, No. 2, pp. 1655–1656, 200.*

H. Seong, et al., "Preparation of Liposomes Containing Dibranched–Amino Acids and Characterization of Their Glucose–Binding Properties," *Polymer Preprints*, 2000, vol. 41, No. 2, pp. 1655–1656.

Shinji Takeoka, et al., "Critical Molecular Weight Effects in the Aggregation of Phospholipid Vesicles Triggered by Water–Soluble Polymers and an Integrated Glycolipid," Macromolecules, 1996, pp. 8132–8136.

* cited by examiner

Primary Examiner—Deborah D. Carr
(74) Attorney, Agent, or Firm—Oblon, Spivak, McClelland, Maier & Neustadt, P.C.

(57) ABSTRACT

Provided is a zwitterionic lipid compound represented by formula (I) given below:

$$\text{-O-C(=O)-(C(R))}_m\text{-C(H)(NH-C(=O)-O-(CH}_2)_p\text{CH}_3)\text{-(CH}_2)_n\text{-C(=O)-O-(CH}_2)_p\text{CH}_3 \quad (I)$$

In formula (I), m and n are independently integers of 1 to 4, p is an integer of 7 to 21, one R is $NH_3^+$, and each other R is H.

5 Claims, No Drawings

ZWITTERIONIC LIPID COMPOUND AND USES THEREOF

CROSS-REFERENCE TO RELATED APPLICATIONS

This is a Continuation Application of PCT Application No. PCT/JP02/08419, filed Aug. 21, 2002, which was not published under PCT Article 21(2) in English.

This application is based upon and claims the benefit of priority from prior Japanese Patent Application No. 2001-254733, filed Aug. 24, 2001, the entire contents of which are incorporated herein by reference.

BACKGROUND OF THE INVENTION

1. Field of the Invention

The present invention relates to a zwitterionic lipid compound and uses thereof, particularly, to a zwitterionic lipid compound, which can be synthesized easily, which has high biocompatibility, and which has high biodegradability, and to the uses thereof utilizing its excellent molecular assembling characteristics such as a surface modifying agent, a dispersion stabilizing agent, a drug carrier and an oxygen carrier.

2. Description of the Related Art

Choline-type phospholipid such as diacylglycerophosphocholine is widely used as a zwitterionic lipid that forms a vesicle. It is known to the art that the zwitterionic lipid forms a stable bilayer membrane by the electrostatic interaction performed between the polar head groups thereof and, thus, the zwitterionic lipid is utilized as a main component of the vesicle.

The properties of the hydrophilic group which the lipid, constituting the membrane of the vesicle, has, are reflected in the physiochemical and physiological properties of the vesicle. For example, if a lipid having polyethylene glycol or saccharide in the hydrophilic part is mixed at an arbitrary ratio, the residence time of the vesicle in the blood is changed. Also, it is possible to increase the accumulation capability of the vesicle on a specified site if various saccharide materials, antibodies, proteins, oligopeptides, etc., are supported on the surface of the vesicle. However, vesicles containing, as the main component, the conventional choline-type phospholipid are used in any of these fields, and a suitable substitute lipid that can be used in place of the choline-type phospholipid has not yet been put into the practical use.

The saturated phospholipid is high in the cost of the raw materials thereof, complicated in synthesis, and necessitates a column in purification, and thus is highly costly. Accordingly, where the vesicle containing the saturated phospholipid as a main component of the membrane is used for administration to the living body, the use of the vesicle is limited to the use as a carrier of an expensive drug that is used at a very small dosage such as an anti-cancer agent. However, since the double chain zwitterionic lipid such as the choline-type lipid forms a stable molecular assembly, the zwitterionic lipid is expected to be used in various fields such as not only the administering agent to the living body in a large amount such as an oxygen carrier but also foods, perfumes, cosmetics, toiletries, and dyes.

Under the circumstances, an object of the present invention is to provide a novel zwitterionic lipid.

BRIEF SUMMARY OF THE INVENTION

As a result of an extensive research conducted in view of the situation described above, the present inventors have succeeded in the synthesis of a double chain zwitterionic lipid compound having an amino group and a carboxyl group in the hydrophilic part. Since the compound can be synthesized very easily and can be purified by utilizing the difference in solubility, the compound can be obtained at a high yield without employing column purification and can be supplied in a large amount. The zwitterionic lipid compound forms a stable bilayer membrane vesicle in an aqueous medium, and a water-soluble substance can be enclosed in the internal phase of the vesicle at high efficiency.

To be more specific, the present invention provides a zwitterionic lipid compound represented by formula (I) given below:

$$\text{-O-}\underset{\underset{O}{\|}}{C}-(\underset{\underset{H}{|}}{C})_m-\underset{\underset{O}{\|}}{C}-\overset{H}{\underset{|}{N}}-\overset{\overset{R}{|}}{\underset{(CH_2)_{\overline{n}}-\underset{\underset{O}{\|}}{C}-O-(CH_2)_pCH_3}{C}}-\overset{\overset{O}{\|}}{\underset{}{C}}-O-(CH_2)_pCH_3 \qquad (I)$$

where m and n are independently integers of 1 to 4, p is an integer of 7 to 21, one R is $NH_3^+$, and each other R is H.

DETAILED DESCRIPTION OF THE INVENTION

The present invention will now be described in detail.

The zwitterionic lipid compound represented by formula (I) can be synthesized as follows.

Firstly, an amino acid represented by formula (A) given below:

$$NH_2-\overset{\overset{COOH}{|}}{\underset{(CH_2)_{\overline{n}}-COOH}{C}} \qquad (A)$$

where n is as defined in formula (I) is reacted with a long chain alcohol represented by formula (B) given below:

$$HO-(CH_2)_pCH_3 \qquad (B)$$

where p is as defined in formula (I), so as to synthesize a long chain alkyl ester of the amino acid, represented by formula (C) given below:

$$NH_2-\overset{\overset{\overset{O}{\|}}{C}-O-(CH_2)_pCH_3}{\underset{(CH_2)_{\overline{n}}-\underset{\underset{O}{\|}}{C}-O-(CH_2)_pCH_3}{|}} \qquad (C)$$

The reaction between the amino acid represented by formula (A) and the long chain alcohol represented by formula (B) can be carried out by, for example, a dehydration condensation method using an acid catalyst, an activated ester method, an acid anhydride method or a mixed acid anhydride method. Particularly, it is desirable to employ the dehydro-condensation method using an acid catalyst, because this method can be worked most easily and the obtained long chain alkyl ester of the amino acid can be refined easily. However, the dehydro-condensation method using an acid catalyst requires heating. Therefore, other methods are employed in the case where the starting materials are unstable against heating.

On the other hand, prepared is an amino acid represented by formula (D) given below:

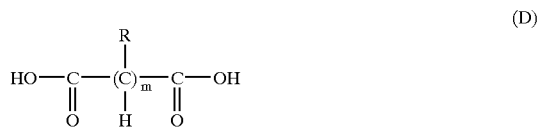
(D)

where m and R are as defined in formula (I), and the amino group and one of the carboxyl groups of the compound represented by formula (D) are protected by the ordinary method. Then, a reaction (amide bond forming reaction) is carried out between the amino acid having the amino group and the carboxyl group protected as above and the amino acid long chain alkyl ester represented by formula (C), followed by removing the protecting groups of the amino group and the carboxyl group so as to obtain the zwitterionic lipid compound of the present invention represented by formula (I).

The reaction between the amino acid having the amino group and the carboxyl group protected as above and the amino acid long chain alkyl ester represented by formula (C) can be carried out by employing, for example, the activated ester method, an acid anhydride method, or a mixed acid anhydride method. It is also possible to carry out a solid phase synthesis by a method similar to the ordinary method of synthesizing peptide.

The synthesizing method of the present invention for synthesizing the zwitterionic lipid compound can be worked easily and permits supplying the desired compound of the zwitterionic lipid compound at a high yield. Also, the zwitterionic lipid compound as synthesized can be purified by utilizing the difference in solubility in the solvent so as to make it unnecessary to employ column purification.

Incidentally, the amino acid used as the raw material has asymmetric carbon atoms, the zwitterionic lipid compound of the present invention can be synthesized by a similar method by using an amino acid in the form of any of the D-form, L-form and a mixture containing the D-form and the L-form at an optional mixing ratio. Where a zwitterionic lipid compound having a high optical isomer purity is required depending on the use of the compound, it is desirable to use an amino acid of D-form or L-form having a high optical isomer purity. Also, it is possible to separate the reaction mixture by using, for example, an optical isomer separating column.

If the zwitterionic lipid compound of the present invention is brought into contact with hydrophilic and hydrophobic interfaces, the hydrophobic groups are oriented toward the hydrophobic surface, and the zwitterionic group is oriented toward the aqueous medium. It follows that the hydrophobic surface can be modified into a hydrophilic surface so as to make it possible to use the zwitterionic lipid compound of the present invention as fillers for separation, and a surface modifying agent for various sensors and the cell culturing substrate. It is also possible to utilize the zwitterionic lipid compound of the present invention as drugs, foods, perfumes, cosmetics, toiletries, an emulsifier of the chemicals used in, for example, a dye, a stabilizing agent, a dispersing agent, a plasticizer, a miscibility promoting agent, a swelling agent, a permeating agent, a viscosity controlling agent.

Where the zwitterionic lipid compound of the present invention is dispersed in an aqueous medium singly or in the form of a mixture with cholesterol or another amphipatic molecule, a stable molecular assembly having a high molecular packing state, i.e., the assembly under, for example, a micellar state, a fibrous state, a disk-like state, a rolled state or in the form of a vesicle, is formed by the hydrophobic interaction between the hydrophobic parts and the electrostatic interaction between the zwitterionic groups. In the case of forming a stable bimolecular membrane vesicle (liposome), the vesicle permits enclosing a water-soluble drug in its inner aqueous phase or permits allowing a recognizing part to be supported on the surface of the liposome membrane so as to make it possible to utilize the vesicle in the drug delivery system. Particularly, if hemoglobin is encapsulated in the internal phase of the vesicle, the vesicle can be utilized as an oxygen carrier.

Where the zwitterionic lipid compound of the present invention is utilized as a main component of the membrane of the vesicle, it is possible to add sterols as another component of the membrane so as to permit the sterols to act as a stabilizing agent. The sterols used in the present invention include, for example, ergosterol and cholesterol. Particularly, it is desirable to use cholesterol as a stabilizing agent. The content of cholesterol is not particularly limited in the present invention. However, it is desirable for cholesterol to be contained in an amount of 5 to 50 mol %, more desirably 20 to 50 mol %, in view of the stability of the vesicle membrane. It should also be noted that, if a negatively charged lipid is mixed as a component of the membrane, the aggregation of the vesicle compounds is suppressed so as to decrease the number of covering layers and, thus, to increase the encapsulating efficiency. Such being the situation, it is possible to add a negatively charged lipid as a component. The negatively charged lipid used in the present invention includes diacyl phosphatidyl glycerol, diacyl phosphatidic acid, diacyl phosphatidyl inositol, diacyl phosphatidyl serine, a fatty acid, a carboxylic acid-type lipid having one carboxylic acid in the hydrophilic part and a plurality of alkyl chains in the hydrophobic part (e.g., a lipid having malonic acid or succinic acid bonded by a covalent bond to the dialkyl derivative of glutamic acid). It is desirable for the content of the negatively charged lipid to fall within a range of 1 to 50 mol %, more desirably 5 to 20 mol %. Further, aggregation of the vesicle can be markedly suppressed by introducing a polyethylene glycol-type lipid into the vesicle membrane so as to increase the residence time of the vesicle in the blood after the administration. Therefore, it is possible to add a polyethylene glycol-type lipid as a membrane component. The polyethylene glycol-type lipid used in the present invention includes, for example, a lipid prepared by allowing polyethylene glycol to be bonded by a covalent bond to the amino group of diacyl phosphatidyl ethanolamine, a lipid prepared by allowing polyethylene glycol to be bonded to the hydroxyl group of a diacyl derivative of glycerol, and a lipid prepared by allowing polyethylene glycol to be bonded by a covalent bond to the carboxyl group or the amino group of a dialkyl derivative of a trifunctional amino acid such as glutamic acid or lysine. It is effective to mix 0.01 to 5 mol % of the polyethylene glycol-type lipid in a lipid mixture prepared by mixing cholesterol or a negatively charged lipid at an optional mixing ratio with the zwitterionic lipid compound of the present invention. Preferably, the mixing amount of the polyethylene glycol-type lipid is 0.1 to 1 mol %. If the mixing amount noted above is smaller than 0.1 mol %, the aggregation suppressing effect is weakened. On the other hand, if the mixing amount noted above is larger than 1 mol %, the encapsulating effect tends to be lowered by the displaced volume effect of the polyethylene glycol chain extending into the internal phase of the vesicle. It is desirable for the polyethylene glycol chain of the polyethylene glycol-type lipid to have a molecular weight falling within a range of about 2,000 to 12,000.

It is possible to use as the aqueous medium noted above pure water, physiological saline, various kinds of buffer solutions, and a solution prepared by dissolving a water-soluble chemical substance in any of these aqueous media. If the pH value of the aqueous medium indicates that the aqueous medium is acidic, the carboxylate anion of the zwitterionic lipid compound is converted into a carboxylic acid. On the other hand, if the pH value of the aqueous medium indicates that the aqueous medium is alkaline, ammonium of the zwitterionic lipid compound is converted into an amine, with the result that the zwitterionic lipid compound ceases to be zwitterionic. However, the pH value is not particularly limited in the case where it is necessary to control the surface charge of the vesicle, or the case where the pH value does not affect the lowering of the stability and the change in the assembling state of the molecules of the zwitterionic lipid compound. Also, where the change in the pH value is utilized for releasing the inclusion of the vesicle by oppositely utilizing the change in the assembling state or for isolating the vesicle by the phase separation from the dispersion medium, it suffices for the pH value to conform with the particular object.

It is desirable for the vesicle formed by using the zwitterionic lipid compound of the present invention to have a particle diameter of 100 to 300 nm. The particle diameter of the vesicle can be controlled by, for example, adding an aqueous medium to a mixed lipid powder for hydration and swelling and by subjecting the swollen hydrated mixture to an incubation hydrating method or by using a boltex mixer, a forced stirrer, an ultrasonic irradiating machine, a homogenizer, a microfluidizer, or a high pressure extruder (extruder), or by freeze thawing. Particularly, the permeability of the filter can be markedly improved by the combination of freeze thawing and the high pressure extruder so as to shorten the treating time and to improve the yield. The aqueous drug that was not encapsulated in the vesicle can be separated from the vesicle by treatment with, for example, gel filtration, centrifugal separation, or an ultrafiltration membrane.

Where a hemoglobin solution is used as an aqueous medium that is encapsulated in the vesicle, it is possible to use a stromer-free hemoglobin solution prepared by subjecting the red blood cells derived from a human being or a cow to hemolysis by the ordinary method, followed by selectively removing the stromer component alone by centrifugal separation or ultrafiltration, a purified hemoglobin solution obtained by isolating hemoglobin, or a recombinant hemoglobin solution that is condensed by ultrafiltration to have a hemoglobin concentration of 10 g/dL or more. Where the vesicle encapsulating hemoglobin is used as an oxygen carrier, it is desirable for the hemoglobin aqueous solution to have a hemoglobin concentration of 20 to 50 g/dL for supplying a sufficiently large amount of oxygen to the living body tissues.

In the present invention, it is possible to add an organic phosphorus compound such as inositol phosphoric acid, or pyridoxal 5' phosphate (PLP) for controlling the affinity of hemoglobin with oxygen. It is also possible to add thiols such as homocysteine and glutathione and water-soluble vitamins. Further, it is possible to add catalase, or a super-oxide dismutase as an activated oxygen removing agent.

The present invention will now be described in more detail with reference to Examples of the present invention. Needless to say, the technical scope of the present invention is not limited at all by these Examples. Incidentally, the chemical structures of compounds (derivatives) 1 to 5 referred to in the following Examples are shown herein later.

EXAMPLE 1

In this Example, a zwitterionic lipid 3 bonded to compound 1 with the hydrophilic part of the α-position carboxylic group of glutamic acid was synthesized as follows.

(A) L-glutamic acid in an amount of 2.96 g (20 mmol) and p-toluenesulfonic acid monohydrate in an amount of 4.56 g (24 mmol) were dissolved in 150 mL of benzene used as a solvent, and the solution was subjected to reflux for one hour while removing the formed water. Then, hexadecyl alcohol was added to the solution in an amount of 10.65 g (44 mmol), and the solution was further subjected to reflux at 105° C. while removing the formed water. After the solvent was removed under a reduced pressure, the residue was dissolved in 150 mL of chloroform. The resultant solution was washed twice with 150 mL of a saturated aqueous solution of sodium carbonate and, then, further washed twice with 150 mL of water. Further, the chloroform layer was obtained and, after the dehydration with sodium sulfate, the solvent was removed under a reduced pressure. The residue was recrystallized at 4° C. from methanol and, after filtration, dried so as to obtain 9.5 g of a white powdery compound 1 at a yield of 80%.

Analytical Result of Compound 1:

Thin layer chromatography (silica gel plate, chloroform/methanol (4/1) (volume/volume): Rf: 0.79 (mono-spot).

Infrared absorption spectrum ($cm^{-1}$): 3385 [$\upsilon_{N-N}$ ($NH_2$)]; 1738[$\upsilon_{C=O}$ (ester)].

$^1$H-NMR spectrum ($CDCl_3$, 500 MHz, δ (ppm)): 0.88 (t, 6H, —$CH_3$); 1.26 (s, 52H, —$CH_2$—$CH_2$—); 1.62 (m, 4H, —CO—O—C—$CH_2$); 1.85, 2.08 (m, 2H, glu β-$CH_2$); 2.46 (m, 2H, glu γ-$CH_2$); 3.46 (m, 1H, glu α-CH); 4.08, 4.12 (tt, 4H, —CO—O—$CH_2$—).

(B) Compound 1 was bonded to glutamic acid having a protected carboxyl group as follows. Specifically, 764 mg (2.52 mmol) of N-t-BOC-L-glutamic acid γ-t-butyl ester and 513 mg (2.52 mmol) of DCC were dissolved in dichloromethane, and the resultant solution was stirred at 4° C. for 30 minutes. Then, the solution thus stirred was dripped into a dichloromethane solution having 1 g (1.68 mmol) of compound 1 and 170 mg (1.68 mmol) of triethylamine dissolved therein. After the reaction mixture solution was stirred at 25° C. for 5 hours, the reactive solution was filtered with a glass filter (G4), and the solvent was removed under a reduced pressure. After the recrystallization from 300 mL of methanol at 4° C., the filtration and the subsequent drying, obtained was 1.15 g of compound 2 having an amino group and glutamic acid having a protected carboxyl group bonded to compound 1 as hydrophilic portions. Compound 2 was obtained as a white solid at a yield of 78%.

Analytical Result of Compound 2:

Thin layer chromatography (silica gel plate, chloroform/methanol (4/1) (volume/volume): Rf: 0.81 (mono-spot).

Infrared absorption spectrum ($cm^{-1}$): 1737 [$\upsilon_{C=O}$ (ester)]; 1665 ($\upsilon_{C=O}$ (amide)); 1570 ($\delta_{N-N}$ (amide)).

$^1$H-NMR spectrum ($CDCl_3$, 500 MHz, δ (ppm)): 0.88 (t, 6H, —$CH_3$); 1.26 (s, 52H, —$CH_2$—$CH_2$—); 1.44, 1.46 (s, 18H, $CH_3$—C—); 1.62 (m, 4H, —CO—O—C—$CH_2$); 1.88–2.25 (m, 4H, glu β-$CH_2$); 2.31–2.44 (m, 4H, glu γ-CH$_2$); 4.06, 4.14 (t, 4H, —CO—O—CH$_2$—); 4.13 (br, 1H, —CH—CONH—); 4.57 (m, 1H, —CH—CO—O—); 5.25 (br, 1H, —O—CO—NH—); 6.90 (d, 1H, amide).

(C) Compound 2 in an amount of 1.15 g (1.30 mmol) was dissolved in 10 mL of TFA and the resultant solution was stirred at 4° C. for 3 hours, followed by adding 50 mL of chloroform to the stirred solution. Then, the reaction system was washed twice with a saturated aqueous solution of sodium carbonate and, then, washed twice with water. After the chloroform layer was dehydrated with anhydrous sodium sulfate, the solvent was removed under a reduced pressure. After the reaction mixture was dissolved in 10 mL of benzene, the components, which were not dissolved, were removed by filtration, and the filtrate was subjected to a freeze drying so as to obtain 0.89 g of zwitterionic lipid 3 as a white solid material with an yield of 92%.

Analytical Result of Compound 3:

Thin layer chromatography (silica gel plate, chloroform/methanol (4/1) (volume/volume): Rf: 0.24 (mono-spot).

Infrared absorption spectrum (cm$^{-1}$): 1739 [$\upsilon_{C=O}$ (ester)]; 1661 ($\upsilon_{C=O}$ (amide)); 1567 ($\delta_{N-N}$ (amide)).

$^1$H-NMR spectrum (CDCl$_3$, 500 MHz, δ (ppm)): 0.88 (t, 6H, —CH$_3$); 1.26 (s, 52H, —CH$_2$—CH$_2$—); 1.61 (m, 4H, —CO—O—CH$_2$); 1.70–2.20 (m, 4H, glu β-CH$_2$); 2.32, 2.41 (m, 4H, glu γ-CH$_2$); 3.40 (m, 1H, —CH—CO—O—); 4.07, 4.12 (t, 4H, —CO—O—CH$_2$—); 4.51 (m, 1H, —CH—CONH—).

MS (FAB) C$_{42}$H$_{79}$O$_7$N$_2$Na: calculated value of 746.6; actually measured value of 747.7 (M$^+$H)$^+$.

EXAMPLE 2

In this Example, zwitterionic lipid 5 bonded to compound 1 with the γ-position carboxylic acid of glutamic acid, which formed a hydrophilic portion, was synthesized as follows:

(A) Compound 1 was bonded to glutamic acid having a protected amino acid and a protected carboxyl group as follows. Specifically, 382 mg (1.26 mmol) of N-t-BOC-L-glutamic acid α-t-butyl ester and 256 mg (1.26 mmol) of DCC were dissolved in dichloromethane, and the resultant solution was stirred at 4° C. for 30 minutes, followed by dripping the stirred solution into a dichloromethane solution having 500 mg (0.84 mmol) of compound 1 and 85 mg (0.84 mmol) of triethylamine dissolved therein. The reaction mixture solution was stirred at 25° C. for 5 hours, followed by filtering the reaction solution with a glass filter (G4) and, then, removing the solvent under a reduced pressure. After recrystallization at 4° C. from methanol, the mixture was filtered and dried so as to obtain 629 mg of a white solid material formed of compound 4 in which glutamic acid having a protected amino group and a protected carboxyl group, which formed a hydrophilic portion, was bonded to compound 1. The yield of compound 4 was 85%.

Analytical Result of Compound 4:

Thin layer chromatography (silica gel plate, chloroform/methanol (4/1) (volume/volume): Rf: 0.84 (mono-spot).

Infrared absorption spectrum (cm$^{-1}$): 1737 [$\upsilon_{C=O}$ (ester)]; 1661 ($\upsilon_{C=O}$ (amide)); 1580 ($\delta_{N-N}$ (amide)).

$^1$H-NMR spectrum (CDCl$_3$, 500 MHz, δ (ppm)): 0.88 (t, 6H, —CH$_3$); 1.26 (s, 52H, —CH$_2$—CH$_2$—); 1.44, 1.47 (s, 18H, CH$_3$—C—); 1.62 (m, 4H, —CO—O—CH$_2$); 1.86–2.22 (m, 4H, glu β-CH$_2$); 2.28–2.45 (m, 4H, glu γ-CH$_2$); 4.05, 4.08 (t, 4H, —CO—O—CH$_2$—); 4.16 (br, 1H, —O—CO—NH—CH—); 4.59 (m, 1H, —CH—CO—O—); 5.20 (br, 1H, —O—CO—NH—); 6.60 (d, 1H, amide).

(B) A solution was prepared by dissolving 629 mg (0.71 mmol) of compound 4 in 10 mL of TFA. The solution thus obtained was stirred at 4° C. for 3 hours and, then, 30 mL of chloroform was added to the stirred solution. The resultant system was washed twice with a saturated solution of sodium carbonate and, then, washed twice with water. After the chloroform layer was dehydrated with anhydrous sodium sulfate, the solvent was removed under a reduced pressure. After the reaction mixture was dissolved in 10 mL of benzene, the components, which were not dissolved, were removed by filtration, and the filtrate was subjected to a freeze drying so as to obtain 488 mg of zwitterionic lipid 5 as a white solid material with an yield of 92%.

Analytical Result of Compound 5:

Thin layer chromatography (silica gel plate, chloroform/methanol (4/1) (volume/volume): Rf: 0.25 (mono-spot).

Infrared absorption spectrum (cm$^{-1}$): 1736 [$\upsilon_{C=O}$ (ester)]; 1650 ($\upsilon_{C=O}$ (amide)); 1588 ($\delta_{N-N}$ (amide)).

$^1$H-NMR spectrum (CDCl$_3$, 500 MHz, δ (ppm)): 0.88 (t, 6H, —CH$_3$); 1.26 (s, 52H, —CH$_2$—CH$_2$—); 1.62 (m, 4H, —CO—O—CH$_2$); 1.94–2.20 (m, 4H, glu β-CH$_2$); 2.40, 2.41 (m, 4H, glu γ-CH$_2$); 3.44 (br, 1H, —CH—CO—O—); 4.06, 4.10 (t, 4H, —CO—O—CH$_2$—); 4.47 (br, 1H, NH$_2$—CH—CH$_2$—).

MS (FAB) C$_{42}$H$_{79}$O$_7$N$_2$Na: calculated value of 746.6; actually measured value of 747.7 (M$^+$H)$^+$.

EXAMPLE 3

Weighed were 150 mg (0.207 mmol) of compound 3, 80 mg (0.207 mmol) of cholesterol, 29 mg (0.041 mmol) of dipalmitoyl phosphatidyl glycerol (DPPG), and 8 mg (0.0014 mmol) of polyethylene glycol-bonded dipalmitoyl phosphatidyl ethanolamine (PEG-DPPEA), and these weighed compounds were put in an eggplant-type flask. Further, 10 mL of benzene was added to the flask while warming the flask so as to dissolve completely the weighed compounds in benzene. The solution was frozen with dry ice-methanol, and the frozen material was mounted on a freeze drying machine for carrying out freeze drying for 10 hours. Then, 25 mL of water for injection containing DPPG and an equimolar amount of NaOH was added to the dried material, and the resultant mixture was stirred by using a magnetic stirrer so as to disperse uniformly the stirred material in the aqueous phase. The dispersion was frozen for 3 minutes with liquid nitrogen, followed by leaving the frozen material to stand for 10 minutes in a constant temperature bath set at 40° C. so as to melt the frozen material. The particular operation was repeated three times, followed by freezing the resultant material with liquid nitrogen. The frozen material was mounted on a freeze drying machine for carrying out a freeze drying for 30 hours so as to obtain a white powdery material of a mixed lipid powder. The mixed lipid powder in an amount of 50 mg was put in an eggplant-type flask. After 5 mL of a carbonylhemoglobin solution having a concentration of 40 g/dL was added to the mixed lipid powder put on the eggplant-type flask, the resultant material was stirred at room temperature for 2 hours by using a magnetic stirrer. The stirred material was put in an Extruder (trade name, manufactured by Nichiyu Liposome Co., Ltd.) having a filter diameter of 25 mm and pressurized with a pressure of 20 kg/cm$^2$ to permit the material to pass successively through acetyl cellulose filters (manufactured by Fuji Photo Film Co., Ltd.) having pore diameters 3.0 μm, 0.45 μm. 0.30 μm and 0.22 μm. The manufactured sample was subjected to ultra-centrifugal separation (100,000 g, 60 minutes) so as to remove hemoglobin that was not included in the internal phase. The sample was irradiated with a white light emitted from a high pressure sodium lamp by using an artificial lung (Capiox-II) so as to permit oxygen to pass through a gas port, thereby allowing oxygen to perform the ligand exchange. A cholesterol quantitative analysis and a hemoglobin (Hb) quantitative analysis were applied to the vesicle containing hemoglobin, which was thus obtained, by using a cholesterol quantitative analysis kit and a hemoglobin quantitative analysis kit available on the market. The total lipid weight was obtained from the cholesterol quantitative analysis, and a ratio of hemoglobin/total lipid was calculated by dividing the hemoglobin weight by the total lipid weight. Also, an oxygen binding and dissociation equilibrium curve was obtained by the measurement with HEMOX-ANALYZER (trade name, manufactured by TCS). Table 1 shows the values thus obtained. For comparison, Table 1 also shows the value of the hemoglobin vesicle that was similarly manufactured by using dipalmitoyl phosphatidyl choline (DPPC) in place of compound 3. Large differences in the properties are not recognized between the present invention and Comparative Example, supporting that it is possible to substitute a choline-type lipid component.

TABLE 1

| | Present Invention | Comparative Example |
|---|---|---|
| Lipid Components (molar ratio) | Compound 3/ Cholesterol/ DPPG/PEG-DPPEA: 5/5/1/0.03 | DPPC/Cholesterol/ DPPG/PEG-DPPEA: 5/5/1/0.03 |
| Particle Diameter (nm) | 275 ± 12 | 281 ± 11 |
| Hb Concentration (g/dL) | 10 | 10 |
| Lipid Concentration (g/dL) | 5.6 | 5.9 |
| [Hb]/[Lipid] | 1.8 | 1.7 |
| Reducing Agent in Vesicle | 5 mM Homocysteine | 5 mM Homocysteine |
| Allosteric Effector (molar ratio) | PLP/Hb:2.5 | PLP/Hb:2.5 |

TABLE 1-continued

| | Present Invention | Comparative Example |
|---|---|---|
| Met-Hb Content (%) | 2.2 | 2.3 |
| Oxygen Affinity $P_{50}$ (Torr) | 32 | 33 |
| Oxygen Transport Efficiency (%) | 35 | 37 |
| Hill Coefficient | 2.1 | 2.1 |

EXAMPLE 4

Compound 5 was dissolved in chloroform (0.5 mM), and 20 μL of chloroform solution was developed by using a micro-syringe on the water surface (pure water) loaded in an LB membrane manufacturing apparatus. The water surface was compressed (28 cm²/min) by moving a barrier until the water surface pressure was increased to reach 25 mN/m so as to form a monolayer membrane. A graphite substrate (1.5 cm×1.5 cm) was brought into contact with the water surface so as to permit the monolayer membrane to be adsorbed on the surface of the graphite substrate. After the graphite substrate was left to stand for 24 hours within a desiccator loaded with silica gel for the drying purpose, the contact angle of a water droplet was measured. The contact angle of the graphite substrate was found to be 152°. On the other hand, the contact angle was found to be 32° on the surface on which the monolayer membrane of compound 5 was adsorbed. This clearly supports that the hydrophobic group of compound 5 was oriented toward the graphite side, and the zwitterionic hydrophilic group was oriented toward the front surface. In other words, it was confirmed that the hydrophobic graphite surface was modified into a hydrophilic surface.

Chemical Structures of Compounds 1 to 5

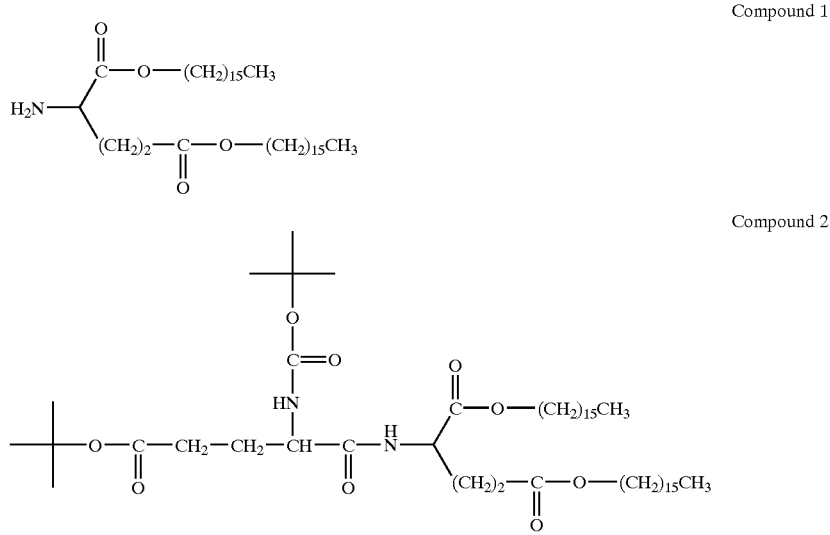

-continued

Compound 3
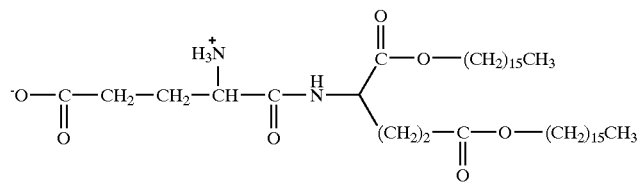

Compound 4
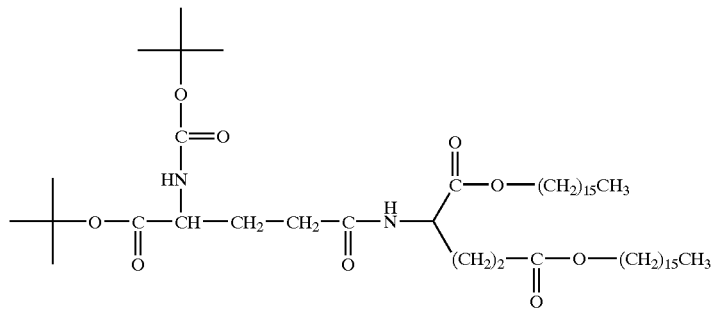

Compound 5
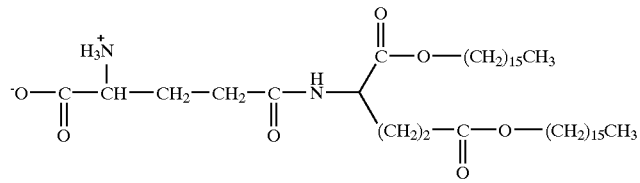

As described above, the present invention provides a double chain zwitterionic lipid compound that can be easily synthesized in a large amount by a simple method.

What is claimed is:

1. An zwitterionic lipid compound represented by formula (I) given below:

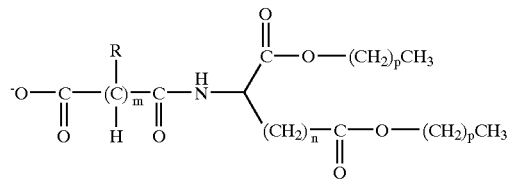

where m is an integer of 3 or 4, n is an integer of 1 to 4, p is an integer of 7 to 21, and R bonded to the fourth carbon atom as counted from the terminal carboxyl carbon atom is $NH_3^+$ and the other R is H.

2. A surface modifying method, comprising
allowing the zwitterionic lipid compound defined in claim 1 to be oriented at the interface at which a hydrophobic substance is brought into contact with an aqueous medium so as to modify the surface of the hydrophobic substance into a hydrophilic surface.

3. A carrier of a water-soluble drug, comprising a vesicle formed by allowing the zwitterionic lipid compound defined in claim 1 to be dispersed in an aqueous medium together with the water-soluble drug.

4. A carrier of a water-soluble drug, comprising a membrane of a lipid containing 40 to 100 mol % of the zwitterionic lipid compound defined in claim 1, a water-soluble drug being included in the inner aqueous phase and a vesicle having a particle diameter of 100 to 300 nm being dispersed in an aqueous medium.

5. The carrier according to claim 4, wherein hemoglobin is included in the inner aqueous phase at a concentration of 10 to 40 g/dL.

* * * * *